(12) United States Patent
Miyata et al.

(10) Patent No.: US 6,387,413 B1
(45) Date of Patent: May 14, 2002

(54) HYALURONIC ACID GEL, A METHOD OF ITS PRODUCTION AND MEDICAL MATERIAL CONTAINING IT

(75) Inventors: Yoshiaki Miyata; Akio Okamoto; Masatoshi Kawata; Kazuhiro Oshima; Masamichi Hashimoto; Kazuhiko Arai, all of Machida; Tomio Sawada, Nagoya, all of (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/463,993

(22) PCT Filed: Aug. 7, 1998

(86) PCT No.: PCT/JP98/03536

§ 371 Date: Jun. 26, 2000

§ 102(e) Date: Jun. 26, 2000

(87) PCT Pub. No.: WO99/10385

PCT Pub. Date: Mar. 4, 1999

(30) Foreign Application Priority Data

Aug. 22, 1997 (JP) .............................. 9-226734
Apr. 27, 1998 (JP) .............................. 10-117564

(51) Int. Cl.[7] .............................. A61K 35/34
(52) U.S. Cl. .................................... 424/548
(58) Field of Search .............. 424/548, 422, 424/423, 426, 427–8, 484, 488; 106/162.2; 352/315.01, 315.1, 315.3

(56) References Cited

U.S. PATENT DOCUMENTS

| | | | |
|---|---|---|---|
| 4,957,744 A | | 9/1990 | Della Valle et al. |
| 5,143,724 A | * | 9/1992 | Leshchiner et al. |
| 5,346,935 A | | 9/1994 | Suzuki et al. |
| 5,616,568 A | * | 4/1997 | Pouyani et al. |
| 5,676,964 A | | 10/1997 | Della Valle et al. |

FOREIGN PATENT DOCUMENTS

| | | |
|---|---|---|
| EP | 0 341 745 B1 | 11/1989 |
| GB | 1086232 | 10/1967 |
| JP | 50-56436 | 5/1975 |
| JP | 5-5881 | 3/1993 |
| JP | 7-102002 | 4/1995 |
| WO | WO 80/00842 | 5/1980 |

OTHER PUBLICATIONS

Zhong et al., Biomaterials, 15(5): 359–365. Biodegradation of hyaluronic acid and derivatives of hyaluonidase, 1994.*
Paparella et al., Irradiation of Polymers: fundamentals and technological applications, Chapter 13, Synthesis of Polysaccharide Chemical Gels by Gamma–Ray Irradiation, pp 180–187. American Chemical Society, Washington, DC, 1996.*

* cited by examiner

Primary Examiner—Christopher R. Tate
Assistant Examiner—Michele C. Flood
(74) Attorney, Agent, or Firm—Oblon, Spivak, McClelland, Maier & Neustadt, P.C.

(57) ABSTRACT

A gel made of hyaluronic acid alone which is hardly soluble in a neutral aqueous solution and which keeps its shape for at least one day in a neutral aqueous solution at 25° C.

10 Claims, 2 Drawing Sheets

HYALURONIC ACID GEL, A METHOD OF ITS PRODUCTION AND MEDICAL MATERIAL CONTAINING IT

BACKGROUND OF THE INVENTION

1. Technical Field

The present invention relates to a novel hyaluronic acid gel and a method of its production, and further, to a biomedical material with good biocompatibility.

2. Background Art

Hyaluronic acid is a linear macromolecular polysaccharide consisting of alternately bonded β-D-N-acetylglucoamine and β-D-glucuronic acid. Hyaluronic acid is found not only in connective tissues of mammals but also in cockscombs and the capsules of *streptococci*. Hyaluronic acid is obtainable not only by extraction from cockscombs and umbilical cords, but also as purified products from the culture broth of *streptococci*.

Natural hyaluronic acid is polydisperse in respect of molecular weight and is known to show excellent biocompatibility even when implanted or injected into the body by virtue of the absence of species and organ specificity. Further, because of the drawbacks of hyaluronic acid in biological application attributable to the easiness of dissolution in water such as the relatively short in vivo residence time, various chemical modifications of hyaluronic acid have been proposed.

A representative of them is a high-swelling crosslinked hyaluronic acid gel obtained by using a bifunctional crosslinker such as divinyl sulfone, a bisepoxide or formaldehyde (U.S. Pat. No. 4,582,865, JP-B-6-37575, JP-A-7-97401 and JP-A-60-130601).

A chemical modification of hyaluronic acid utilizing the solubility of tetrabutylammonium hyaluronate in organic solvents such as dimethyl sulfoxide has been disclosed, too (JP-A-3-105003). Formation of ester linkages between the carboxyl groups and the hydroxyl groups in hyaluronic acid by treating tetrabutylammonium hyaluronate with triethylamine and 2-chloro-1-methylpyridinium iodide in dimethyl sulfoxide has also been disclosed (EP-A-0341745A1).

Further, as an approach to insolubilization of hyaluronic acid in water without using covalently binding chemicals, preparation of a hyaluronic acid-polymer complex by ionically bonding hyaluronic acid and a polymer having an amino or imino group via the carboxyl groups in hyaluronic acid and the amino or imino group in the polymer has been disclosed (JP-A-6-73103).

It is known that a hyaluronic acid aqueous solution forms a so-called putty gel by jellying when acidified, for example, to pH 2.0–2.7, but no putty gel is formed at a pH below 2. The putty gel is differentiated from the hyaluronic acid gel according to the present invention by its quick dissolution in a neutral aqueous solution.

As another approach, production of a hyaluronic acid gel from a hyaluronic acid aqueous solution in the presence of 20–80 wt % of a water-miscible organic solvent at pH 2.0–3.8 has been disclosed (JP-A-5-58881). However, it is also disclosed that the resulting hyaluronic acid gel dissolves in water with no coating on it.

Further, some general methods of producing polymer gels by repeatedly freezing and thawing aqueous solutions of polymers represented by polyvinyl alcohol and glucomannan have been proposed (JP-A-57-190072 and JP-A-5-161459).

Although freezing-thawing and freeze-drying are widely used as general techniques for purifying or preserving hyaluronic acid or biogenic samples containing hyaluronic acid, no report has been made on formation of a hyaluronic acid gel by such techniques yet because they are usually used under neutrality control.

Hyaluronic acid has extraordinarily high viscosity and good moisture retentivity, and is intrinsically devoid of antigenicity and highly biocompatible. Therefore, it is used as a therapeutic medicine for osteoarthritis and as a supplementary material in ophthalmic surgery.

Use of hyaluronic acid itself as a postoperative adhesion preventive has also been studied. However, hyaluronic acid does not have much effect due to the relatively short in vivo residence time and diffusively drains away from the wound surface in a short time due to its water solubility (Journal of Gynecologic Surgery vol.7, No.2, 97–101(1991)).

Modification of carboxymethyl cellulose and sodium hyaluronate with a carbodiimide crosslinker on the basis of JP-A-5-508161 and JP-A-6-508169 afforded the development of an adhesion preventive film "Seprafilm" (Genzyme).

Despite attempts to utilize the outstanding biocompatibility intrinsic to hyaluronic acid to the maximum, no hyaluronic acid gel usable as a biocompatible biomedical material with a long in vivo residence time has been developed yet without any chemical crosslinkers or chemical modifiers or formation of complexes with cationic polymers.

The present inventors have conducted extensive research on the physicochemical properties of hyaluronic acid itself and consequently have found that a hyaluronic acid gel can be obtained by freezing and thawing at least once a hyaluronic acid aqueous solution adjusted to a specific pH. They have also found that the hyaluronic acid gel thus obtained dissolves in water very slowly.

Conventional modifications of hyaluronic acid have an inevitable problem of extra risks such as toxicity and bio-incompatibility intrinsic to the modifications because of the use of chemical reactants despite numberless efforts.

For example, chemical modification, crosslinking or ionic treatment of hyaluronic acid with a metal salt may afford adhesion preventives with improved in vivo persistency. However, the resulting adhesion preventives no longer retain the structure of natural hyaluronic acid and are not essentially the same as natural hyaluronic acid in respect of physiological effects, biocompatibility and safety inclusive of toxicity, because of the crosslinkers or metals covalently or ionically bound in the hyaluronic acid molecules. In addition, it has been difficult to completely circumvent the problems of the residual toxicity of these crosslinkers and the risk of decomposition products of crosslinkers to the body.

DISCLOSURE OF THE INVENTION

The present inventors have found that the hyaluronic acid gel according to the present invention has ideal biocompatibility and persistency as a biomedical material, particularly ideal biocompatibility and persistency as an adhesion preventive and markedly prevents postoperative adhesion. The present inventors have accomplished the present invention on the basis of this discovery.

The present invention provides (1) a gel made of hyaluronic acid alone which is hardly soluble in a neutral aqueous solution, (2) the hyaluronic acid gel according to (1), which keeps its shape for at least one day in a neutral aqueous solution at 25° C., (3) the hyaluronic acid gel according to (1), which dissolves in a neutral aqueous solution at 25° C.

in one day to a degree of dissolution of at most 50%, (4) the hyaluronic acid gel according to (1), which dissolves in a neutral aqueous solution at 37° C. in 12 hours to a degree of dissolution of at most 50%, (5) the hyaluronic acid gel according to (1), which dissolves to yield solubilized hyaluronic acid having a branched structure and partly containing a molecular weight fraction with a branching degree of at least 0.5, when treated under accelerating conditions for acid hydrolysis of hyaluronic acid, (6) the hyaluronic acid gel according to (1), which is formed by freezing and then thawing an aqueous solution of hyaluronic acid at pH 3.5 or below, (7) a method of producing the hyaluronic acid gel according to (6), which comprises adjusting an aqueous solution of hyaluronic acid to pH 3.5 or below, and freezing and thawing the solution at least once, (8) a biomedical material containing a gel made of hyaluronic acid alone which satisfies the following requirements (a) and (b): (a) the hyaluronic acid gel dissolves in a neutral aqueous solution at 25° C. in one day to a degree of dissolution of at most 50%, and (b) the gel dissolves to yield solubilized hyaluronic acid having a branched structure and partly containing a molecular weight fraction with a branching degree of at least 0.5, when treated under accelerating conditions for acid hydrolysis of hyaluronic acid, (9) the biomedical material according to (8), wherein the gel made of hyaluronic acid alone is sheet-like, filmy, flaky, spongy, massive, fibrous or tubular, (10) a biomedical material containing a hyaluronic acid gel and un-gelled hyaluronic acid, wherein the hyaluronic acid gel dissolves in a neutral aqueous solution at most 50%, and the hyaluronic acid gel dissolves to yield solubilized hyaluronic acid having a branched structure and partly containing a molecular weight fraction with a branching degree of at least 0.5, when treated under accelerating conditions for acid hydrolysis of hyaluronic acid, (11) a biomedical material containing a hyaluronic acid gel made of hyaluronic acid alone which is sheet-like, filmy, spongy, massive, fibrous or tubular and un-gelled hyaluronic acid, and (12) the biomedical material according to any one of (8) to (11), which is an adhesion preventive.

BEST MODE FOR CARRYING OUT THE INVENTION

Figure 1:
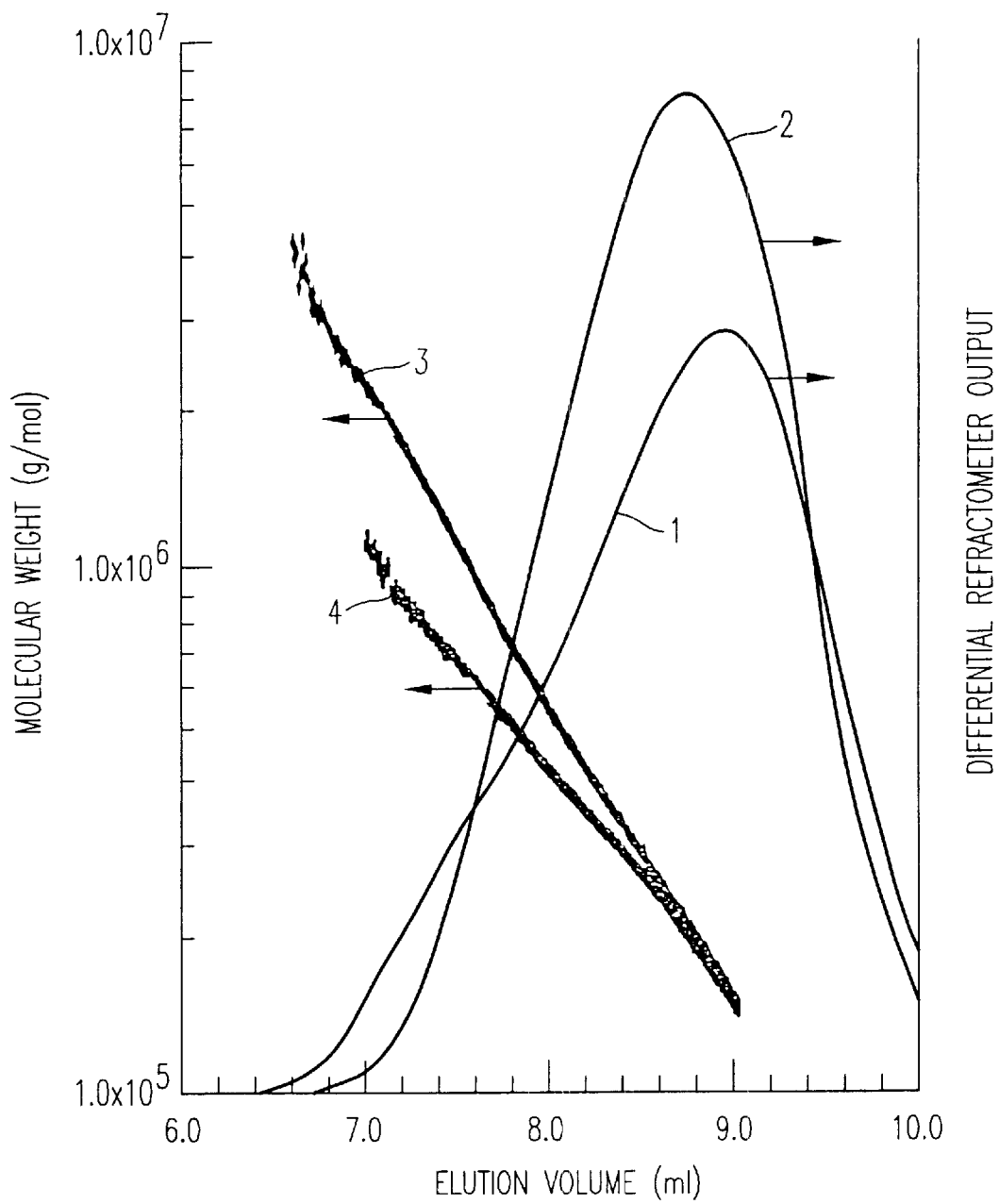
FIG. 1 is a graph that shows the comparison between GPC chromatograms and the molecular weights of the respective fractions obtained in Example 8 and Comparative Example 6.

Now, the present invention will be described below in detail.

In the present invention, hyaluronic acid obtained by extraction from animal tissues or by fermentation may be used without any restriction on its source.

The strain used in fermentation is preferably a hyaluronic acid-producing microorganism isolated from nature such as the genus Streptococcus or a mutant which steadily produces hyaluronic acid in high yield such as *Streptococcus equi* FM-100 (accession number 9027 given by National Institute of Bioscience and Human-Technology) disclosed in JP-A-63-123392 or *Streptococcus equi* FM-300 (accession number 2319 given by National Institute of Bioscience and Human-Technology) disclosed in JP-A-2-234689. Pure hyaluronic acid obtained from cultures of the above-mentioned mutants may be used.

Gel is defined as "a polymer having a three-dimensional network structure insoluble in any solvent or its swollen product" by Encyclopedia of Polymer (Kobunshi Jiten) New Edition (published by Asakura Shoten, 1988). It is also defined as "a jellied product of a sol (a colloidal solution)" by Encyclopedia of Science and Chemistry (Rikagaku Jiten) Forth Edition (published by Iwanami Shoten, 1987).

The hyaluronic acid gel according to the present invention is characterized in that it is hardly soluble in a neutral aqueous solution, and when the hyaluronic acid gel is put in a neutral aqueous solution, it dissolves with significantly greater difficulty than un-gelled hyaluronic acid does. The difficulty in dissolution is defined by the persistence of the shape of the gel and the solubility of the gel in a neutral aqueous solution at 25° C. and the solubility of the gel in a neutral aqueous solution at 37° C. The neutral aqueous solution means a buffered physiological saline adjusted to pH 7.

The hyaluronic acid gel according to the present invention is also characterized in that it dissolves quickly in an aqueous alkaline buffer solution, for example, at pH 11.

The hyaluronic acid gel according to the present invention is a polymer having a three dimensional network structure or its swollen product. The three dimensional network structure is made of crosslinked hyaluronic acid.

The hyaluronic acid gel according to the present invention can be solubilized through degradation by treatment under accelerating conditions for acid hydrolysis of hyaluronic acid. When the solubilized hyaluronic acid retains the crosslinked structure, it is distinguished as branched hyaluronic acid from linear hyaluronic acid according to the theory of polymer solution. Hyaluronic acid itself is a linear polymer and known to have no branches (Biochemistry of Polysaccharides I Chemistry Version (Tato Seikagaku I Kagaku-hen) published by Kyoritus Shuppan, 1969).

The accelerating conditions for acid hydrolysis of hyaluronic acid according to the present invention are preferably such that the pH of the aqueous solution is 1.5 and the temperature is 60° C. It is well known that cleavage of the main chain of hyaluronic acid through hydrolysis of glycosidic bonds is remarkably accelerated in an acidic or alkaline aqueous solution as compared with that in a neutral aqueous solution (Eur. Polym. J. Vol32, No8, p1011–1014, 1996). In addition, acid hydrolysis is accelerated at a higher temperature.

The reaction time for the accelerated hydrolysis of a hyaluronic acid gel according to the present invention heavily depends on the structure of the hyaluronic acid gel such as the molecular weight or molecular weight distribution of the hyaluronic acid as the raw material, and degree of crosslinking of the gel.

The reaction conditions are selected so that the proportion of the solubilized hyaluronic acid and the branching degree are large. If the reaction conditions are too mild or too severe, the branching degree is difficult to measure, because the proportion of the solubilized hyaluronic acid is small under mild conditions, and on the other hand, the molecular weight of the solubilized hyaluronic acid is too small under severe reaction conditions. Besides, the possibility of destruction of the branch points themselves increases.

As to the reaction conditions, a preferable reaction time is such that the visually recognizable hyaluronic acid gel disappears almost completely or such that the proportion of the solubilized hyaluronic acid reaches 50% or above.

For the measurement of the molecular weight and branching degree of the solubilized hyaluronic acid, the GPC-MALLS method, which uses a differential refractometer and a multi-angle laser light scattering detector (MALLS) as detectors for gel permeation chromatogram (GPC), the GPC-LALLS method, which uses a differential refractometer and a low angle laser light scattering detector as detectors for GPC, and the GPC-viscosity method, which uses a differential refractometer and a viscometer as detectors for GPC, may be mentioned.

In the present invention, the molecular weights and branching degrees of the fractions separated by GPC according to molecular weight are measured on-line continuously by the GPC-MALLS method. The GPC-MALLS method allows continuous measurement of the molecular weight and radius of gyration of each fraction separated by GPC. In the GPC-MALLS method, for calculation of the branching degree, two methods are available: the radius of gyration method which compares the correlation between the molecular weight and radius of gyration of the fractionated solubilized hyaluronic acid with the correlation of the molecular weight and radius of gyration of fractionated linear hyaluronic acid as a control, and the elution volume method which compares the molecular weight of each fraction of the solubilized hyaluronic acid with the molecular weight of a fraction at the same elution volume of linear hyaluronic acid as a control.

In the present invention, the branching degree was measured by the elution volume method. The branching degree is the number of branch points in one polymer chain of the solubilized hyaluronic acid and plotted against the molecular weight of the solubilized hyaluronic acid.

For determination of the molecular weight and radius of gyration of each fraction, the Zimm plot of the equation (1) at finite concentration was used. The molecular weight was calculated from the extrapolation to scattering angle 0°, and the radium of gyration was calculated from the angle-dependent initial slope in accordance with the following equations.

$$\frac{K_c}{R(\theta)} = \frac{1}{MP(\theta)} + 2A_2 c + \ldots \quad (1)$$

$$P(\theta)^{-1} = 1 + 1/3 \cdot k^2 \langle S^2 \rangle + \ldots$$

$$k = \frac{4\pi}{\lambda} \sin(\theta/2)$$

wherein M is the molecular weight, $\langle S^2 \rangle$ is the mean square radius of gyration, K is an optical constant, $R(\theta)$ is the reduced excess scattering intensity, c is the polymer concentration, $P(\theta)$ is the particle scattering function, $\lambda$ is the wavelength of the laser beam in the solution, and $A_2$ is the second virial coefficient, 0.002 ml·mol/g² for hyaluronic acid. c is calculated from the output of a differential refractometer, based on the differential refractive index increment of a hyaluronic acid aqueous solution (dn/dc: 0.153 ml/g).

In the GPC-MALLS method, the molecular weight and mean square radius of gyration are calculated from the reduced excess scattering intensity, and therefore, the measuring accuracy depends on the reduced excess scattering intensity. Equation (1) relates the reduced excess scattering intensity to both the concentration and the molecular weight. Accordingly, the sample concentration and the injection volume must be determined in accordance with the molecular weight of the sample. When the GPC column for molecular weight fractionation is selected, the maximum sample concentration and injection volume should be selected so that the GPC column is not overloaded.

In the elution volume method, the branching degree of each fraction was calculated in accordance with equation (2) given below. The shrinkage factor, g, is determinable from the molecular weights of a branched polymer, $M_b$, and a linear polymer, $M_1$, in fractions at the same elution volume.

$$g = (M_1/M_b)^{(a+1)/e} \quad (2)$$

Here, a is the Mark-Houwink constant, which is 0.78 for hyaluronic acid, and e is the draining factor, which is defined as 1.

When randomly branched polymer (long chain branching, tetrafunctional) are assumed, the number of branches in one polymer chain, B, (branching degree) can be calculated in accordance with equation (3) given below.

$$g = \frac{1}{\left[\left[1+\frac{B}{6}\right]^{0.5}\left[\frac{4B}{3\pi}\right]\right]^{0.5}} \quad (3)$$

Measurement of branching degree by the elution volume method is the same as measurement of branching degree by the GPC-LALLS method, details of which are found in Size Exclusion Chromatography (Kyoritsu Shuppan, 1991). Solubilized hyaluronic acid was diluted with the GPC eluent for concentration adjustment and filtered through a membrane filter of 0.2 $\mu$m before measurement.

If the hyaluronic acid gel according to the present invention has a crosslinked structure which is stable under accelerating conditions for acid hydrolysis of hyaluronic acid, a branched structure is recognized in the solubilized hyaluronic acid according to the theory of polymer solution.

In the present invention, by hyaluronic acid alone, it is meant that no chemical crosslinker or chemical modifier is used other than hyaluronic acid, and that hyaluronic acid is not in the form of a complex with a cationic polymer.

The chemical crosslinker for hyaluronic acid means a polyvalent compound which reacts with the carboxylic group, hydroxyl group or acetamido group in hyaluronic acid to form a covalent bond. For example, a polyvalent epoxy compound such as polyglycidyl ether, divinyl sulfone, formaldehyde, phosphorus oxychloride, the combination of a carbodiimide compound and an amino acid ester, and the combination of a carbodiimide compound and a dihydrazide compound may be mentioned. A chemical crosslinker reacts with hyaluronic acid to form a three-dimensional network structure.

The chemical modifier for hyaluronic acid means a compound which reacts with the carboxylic group, hydroxyl group or acetamido group in hyaluronic acid to form a covalent bond. For example, the combination of acetic anhydride and concentrated sulfuric acid, the combination of trifluoroacetic anhydride and an organic acid and an alkyl iodide compound may be mentioned. It makes the hydrophilic groups in hyaluronic acid hydrophobic and thereby lowers the solubility of hyaluronic acid.

The cationic polymer which forms a complex with hyaluronic acid means a polymer which forms a complex through an ionic bond between the carboxylic groups in hyaluronic acid and the amino or imino group in the polymer, and chitosan, polylysine, polyvinylpyridine, polyethyleneimine and polydimethylaminoethylmethacrylate may be mentioned, for example. A cationic polymer and hyaluronic acid form a complex insoluble in water.

On the other hand, substances which do not directly induce introduction of a crosslinked structure into hyaluronic acid or make hyaluronic acid insoluble or hardly soluble may be added when the hyaluronic acid gel according to the present invention is prepared. Materials as biocompatible as hyaluronic acid such as chondroitin sulfate and carboxymethyl cellulose, may be mixed or incorporated to give a hyaluronic acid gel without any restriction.

Further, in preparation of a hyaluronic acid gel, pharmacologically or physiologically active substances may be added to give a hyaluronic acid gel containing such substances without any restriction.

The molecular weight of the hyaluronic acid to be used in the present invention is preferably within the range of from about $1 \times 10^5$ to about $1 \times 10^7$ Da. Hyaluronic acid having a higher molecular weight may also be used after the molecular weight is lowered into this range by treatment such as hydrolysis.

In the present invention, the concept of hyaluronic acid is used so as to include its alkali metal salts such as sodium, potassium and lithium salts, too.

The hyaluronic acid aqueous solution used in the present invention is obtained by stirring a mixture of powdery hyaluronic acid and water. The hyaluronic acid concentration is preferably 5.0 wt % or less in view of handling of the aqueous solution.

When hyaluronic acid having a molecular weight of $2 \times 10^6$ Da or more is used, the concentration is preferably 2.5 wt % or less.

For pH adjustment of a hyaluronic acid aqueous solution, any acid that can adjust the pH to 3.5 or below may be used. Preferably, a strong acid such as hydrochloric acid, nitric acid and sulfuric acid is used to decrease the amount of an acid.

The pH of a hyaluronic acid aqueous solution is adjusted so that a sufficient proportion of the carboxylic groups in hyaluronic acid undergoes protonation. The dissociation constant of hyaluronic acid in the acid form is $\log K_0 = 4.25$ when hyaluronic acid is diluted to indefinite concentrations (Acta Chemica Hungarica-Models in Chemistry 129(5), 671–683, 1992). In the present invention, it is necessary to adjust the pH to 3.5 or below, preferably to 2.5 or below, although the final pH is set depending on the type of the counterinon in the hyaluronic acid salt, the molecular weight of hyaluronic acid, the concentration of the aqueous solution, conditions of freezing and thawing, and the properties of the resulting gel such as strength.

With respect to freezing-thawing, a procedure comprising freezing the prepared acidic hyaluronic acid aqueous solution in an appropriate vessel at a predetermined temperature and then thawing it at a predetermined temperature is carried out at least once. Although the freezing and thawing temperatures and times may be appropriately set depending on the size of the vessel and the volume of the aqueous solution so that the acidic hyaluronic acid solution freezes and thaws, it is generally preferred that the freezing temperature is not higher than the ice point, and the thawing temperature is not lower than the ice point.

It is particularly preferred that the freezing temperature is −5° C. or below, and the thawing temperature is 5° C. or above, to shorten the freezing and thawing times. There is no restriction on the freezing and thawing times so long as they are longer than it takes to complete freezing and thawing at the temperatures.

The number of times the procedure comprising freezing and then thawing the prepared acidic hyaluronic acid aqueous solution is repeated, depends on the molecular weight of hyaluronic acid to be used, the concentration and pH of the aqueous solution, the freezing and thawing temperatures and times and various properties of the resulting gel such as strength. Usually, it is preferred to repeat the procedure at least once.

Further, the freezing and thawing temperatures and times may be changed every time the freezing-thawing is repeated.

From the hyaluronic acid gel obtained by freezing and thawing a prepared acidic hyaluronic acid aqueous solution, the acid component added for the acidification has to be removed in order to prevent acid hydrolysis of hyaluronic acid. For removal of the acid component, the gel is usually washed with an aqueous solvent, for example, water, physiological saline or a phosphate buffer, preferably physiological saline or a phosphate buffer. There is no restriction on the aqueous solvent so long as it does not functionally impair the hyaluronic acid gel.

Although there is no particular restriction on the washing method, a batch method, a filtration method or a method in which a solvent is passed through a loaded column is usually used. The washing conditions, inclusive of the volume of the washing solvent and the times of washing, may be selected considering the shape and the use of the hyaluronic acid gel so that the concentration of the component to remove can be lowered to the desired level or below.

The washed hyaluronic acid gel is used as a biomedical material in an immersed state with a solvent, in a wet state with a solvent or in a dry state after air-drying, vacuum drying or freeze drying depending on the use.

With a view to shaping the hyaluronic acid gel, by selecting the vessel and the procedure when the prepared acidic hyaluronic acid aqueous solution is frozen in its preparation, a hyaluronic acid gel of desired shape such as a sheet-like, filmy, flaky, spongy, massive or tubular shape can be obtained. For example, freeze casting on a plate affords a film or a sheet, and freezing-thawing in an organic solvent immiscible with water under vigorous stirring affords flakes.

Preparation of a hyaluronic acid gel may be followed by post-treatment such as mechanical fragmentation, rolling or spinning to make the gel into fine flakes, a film or the like. However, a hyaluronic acid gel of desired shape can be obtained without any special treatment for shaping by appropriately selecting the production conditions. For example, a prepared acidic hyaluronic acid aqueous solution having a hyaluronic acid concentration of 0.1% or less, preferably 0.05% or below yields a fine fibrous hyaluronic acid gel after freezing-thawing.

The hyaluronic acid gel obtained according to the present invention may be used as a general biodegradable biomedical material in any fields wherein hyaluronic acid is used without any particular restriction. It may be used for, for example, an adhesion preventive, a carrier for a pharmacologically active substance, a wound dressing, an artificial skin, a replacement vital tissue repairer, a joint injection, a surgical suture, a hemostatic material, an artificial organ, an artificial extracellular matrix, an artificial basement membrane or biomedical products such as medical tools and devices for diagnostic or therapeutic use or medicinal compositions.

Shaped products of a hyaluronic acid gel may be used in combinations of different shapes let alone in a single shape and are expected to have a stronger effect when mixed with or used in combination with an un-gelled hyaluronic acid.

For example, the combined use of a hyaluronic acid gel sheet and a hyaluronic acid solution as an adhesion preventive after peritoneotomy is expected to have both a regional effect and an extensive intraperitoneal effect.

Also, a mixture of a flaky hyaluronic acid gel and a hyaluronic acid solution is expected to have a rapid effect and a delayed effect as a joint injection.

Now, the usefulness of the hyaluronic acid gel obtained according to the present invention as a biomedical material will be described with reference to the use as a slow release carrier for a pharmacologically active substance.

The hyaluronic acid gel obtained according to the present invention can be used as a carrier which slowly releases a pharmacologically active substance encapsulated in its structure. In this case, by controlling the properties represented by degradability and shape of the hyaluronic acid gel in accordance with the kind of the pharmacologically active substance, the mode of use, the application site and the required residence time, it is possible to adapt the gel to various pharmacologically active substances and various modes of use.

When formulated appropriately, a pharmaceutical which can release a pharmacologically active substance in a desired way can be obtained. The slow release pharmaceutical may be administered orally, percutaneously, permucocutaneously, by injection or by implantation. Next, the adhesion preventive of the present invention will be described below.

The adhesion preventive made of a hyaluronic acid gel obtained according to the present invention is a sheet-like, filmy, flaky, massive, fibrous or tubular material for surgical use. With respect to the mode of use, it is preferred to directly apply a filmy or sheet-like material to a part subjected to surgery. It is also preferred to apply a fine flaky material by injection to a part subjected to surgery. It is also preferably to peritoneoscopically apply a gel or a filmy material to a part subjected to surgery.

Further, an adhesion preventive made of a hyaluronic acid gel encapsulating a physiologically active substance can be obtained by mixing a prepared acidic hyaluronic acid solution and a physiologically active substance and then freezing and thawing the mixture.

An adhesion preventive made of a hyaluronic acid gel is applicable to any animals that can suffer from adhesion and favorably prevents postoperative adhesion in mammals, especially in the human.

It is effective wherever it may be administered in the body, for example, to various intaperitoneal and intrathoracic organs, peritenoneums, the skull, nerves and eyeballs in peritoneotomy, gynecological surgery and thoracotomy, to tendons and ligaments in orthopedic surgery and to the dura mater in neurosurgery.

The adhesion preventive made of a hyaluronic acid gel obtained according to the present invention may be administered at any time during or after operations so long as postoperative adhesion can be prevented, but preferably at the last of an operation.

Now, the present invention will be described in further detail with reference to Examples. However, the present invention is by no means restricted to these specific Examples.

EXAMPLE 1

Sodium hyaluronate with a molecular weight of $2 \times 10^6$ Da was dissolved in distilled water to give a 1 wt % hyaluronic acid aqueous solution. The pH of the hyaluronic acid aqueous solution thus obtained was 6.0. The pH of the aqueous solution was adjusted to 1.5 with 1N hydrochloric acid. A 15 ml portion of the acidic hyaluronic acid aqueous solution was put in a 30 ml glass bottle and placed in a refrigerator set at $-20°$ C. for 16 hours and then thawed at $25°$ C. to give a spongy hyaluronic acid gel.

EXAMPLE 2

In Example 1, the hyaluronic acid concentration was changed to 0.1 wt % in the preparation of the hyaluronic acid aqueous solution, and the same procedure as in Example 1 was followed to give a spongy hyaluronic acid gel.

EXAMPLE 3

In Example 1, hyaluronic acid with a molecular weight of $6 \times 10^5$ Da was dissolved to give a hyaluronic acid aqueous solution. After the same adjustment operation as in Example 1, the aqueous solution thus obtained was placed in a refrigerator set at $-20°$ C., and at least 6 hours of freezing and at least 2 hours of thawing at $25°$ C. were repeated 5 times to give a spongy hyaluronic acid gel.

EXAMPLE 4

In Example 1, the freezing temperature was set at $-10°$ C. Freezing at $-10°$ C. for 77 hours and subsequent thawing at $25°$ C. gave a spongy hyaluronic acid gel.

EXAMPLE 5

In Example 1, an acidic hyaluronic acid aqueous solution at pH 2.5 was prepared from a 0.4 wt % hyaluronic acid aqueous solution. A 15 ml portion of the acidic hyaluronic acid aqueous solution was put in a 30 ml glass bottle and placed in a refrigerator set at $-20°$ C. At least 6 hours of freezing and at least 2 hours of thawing at $25°$ C. were repeated 8 times to give a partially spongy hyaluronic acid gel.

COMPARATIVE EXAMPLE 1

In Example 1, a hyaluronic acid aqueous solution was frozen and thawed repeatedly 8 times without pH adjustment. No change happened to the hyaluronic acid aqueous solution, namely gelation did not occur.

COMPARATIVE EXAMPLE 2

The hyaluronic acid aqueous solution prepared in Example 1 was air-dried at $60°$ C. to give a cast film of about 100 $\mu$m thick, which was subjected to a solubility test for hyaluronic acid gels.

COMPARATIVE EXAMPLE 3

The hyaluronic acid aqueous solution prepared in Example 1 was frozen at $-20°$ C. and freeze-dried to give a hyaluronic acid sponge, which was subjected to a solubility test for hyaluronic acid gels.

EXAMPLE 6

Solubility Test for Hyaluronic Acid Gels

A phosphate buffer was added to physiological saline at a concentration of 50 mM to give a phosphate buffer-physiological saline at pH 7.0. The spongy hyaluronic acid gels obtained in the preceding Examples were washed with distilled water and drained on filter paper. The hyaluronic acid gels were immersed in 50 ml of the phosphate buffer-physiological saline based on 150 mg of dry hyaluronic acid in the gels.

The solids of hyaluronic acid obtained in Comparative Examples were immersed in 50 ml of the phosphate buffer-physiological saline based on 150 mg of dry weight.

The degree of dissolution of hyaluronic acid in the phosphate buffer-physiological saline at $25°$ C. was obtained from the concentration of hyaluronic acid in the phosphate buffer-physiological saline.

Namely, the solubility of a hyaluronic acid gel in a neutral aqueous solution at $25°$ C. is defined according to this test.

Measurement of Hyaluronic Acid Concentration

The concentration of hyaluronic acid in the phosphate buffer-physiological saline was obtained from the area of a GPC peak by using a differential refractometer as a detector.

As described above, the solubility test was actually carried out on the hyaluronic acid gels obtained in Examples 1 to 4 and the solids of hyaluronic acid obtained in Comparative Examples 2 and 3. The results were tabulated in Table 1 together with the results of observation of the shapes of the hyaluronic acid gels by the naked eye.

For example, in Test No.1, the degree of dissolution of the hyaluronic acid gel obtained in Example 1 was found to be 3% after 1 day, 5% after 4 days and 6% after 7 days. Namely, 94% of the hyaluronic acid remained even after 7 days. The spongy shape was also maintained. In Test No.5, the degree of dissolution of the cast film of about 100 μm thick obtained in Comparative Example 2 was found to be 100% after 1 day, which indicates complete dissolution. It remained completely dissolved after 4 days and after 7 days.

Thus, it was found that the solids of hyaluronic acid obtained in Comparative Examples dissolved in water quite quickly (Tests Nos.5 to 6), whereas the hyaluronic acid gels obtained according to the present invention dissolved very slowly (for example, Tests Nos. 1 to 4).

These results suggest that the hyaluronic acid gel obtained according to the present invention has a long in vivo residence time.

TABLE 1

Degree of dissolution (upper column %) and shape (lower column) of hyaluronic acid gel

| Test No | After 1 day | After 4 days | After 7 days | After 14 days | Remarks |
|---|---|---|---|---|---|
| 1 | 3 | 5 | 6 | 10 | Example 1 |
|   | Spongy | Spongy | Spongy | Spongy |   |
| 2 | 2 | 4 | 6 | 15 | Example 2 |
|   | Spongy | Spongy | Spongy | Spongy |   |
| 3 | 9 | 14 | 28 | 38 | Example 3 |
|   | Spongy | Spongy | Spongy | Spongy |   |
| 4 | 3 | 5 | 7 | 11 | Example 4 |
|   | Spongy | Spongy | Spongy | Spongy |   |
| 5 | 100 (Completely dissolved) | The same condition as after 1 day | The same condition as after 1 day | The same condition as after 1 day | Comparative Example 2 |
| 6 | 100 (Completely dissolved) | The same condition as after 1 day | The same condition as after 1 day | The same condition as after 1 day | Comparative Example 3 |

COMPARATIVE EXAMPLE 4

A powder of sodium hyaluronate with a molecular weight of 2×10⁶ Da was subjected to a solubility test for hyaluronic acid gels.

COMPARATIVE EXAMPLE 5

A powder of sodium hyaluronate with a molecular weight of 2×10⁶ Da was press-molded into discoidal pellets. The pellets were subjected to a solubility test for hyaluronic acid gels.

EXAMPLE 7

Solubility Test for Hyaluronic Acid Gels

A phosphate buffer was added to physiological saline to a concentration of 50 mM to give a phosphate buffer-physiological saline at pH 7.0. The spongy hyaluronic acid gels obtained in the preceding Examples were washed with distilled water and drained on filter paper. The hyaluronic acid gels were immersed in 50 ml of the phosphate buffer-physiological saline based on 20 mg of dry hyaluronic acid in the gels.

The solids of hyaluronic acid obtained in Comparative Examples were immersed in 50 ml of the phosphate buffer-physiological saline based on 20 mg of dry weight.

The degree of dissolution of hyaluronic acid in the phosphate buffer-physiological saline at 37° C. with stirring was obtained from the concentration of hyaluronic acid in the phosphate buffer-physiological saline.

Namely, the solubility of a hyaluronic acid gel in a neutral aqueous solution at 37° C. is defined according to this test.

As described above, a solubility test was actually carried out on the hyaluronic acid gels obtained in Examples 1 to 4 and the solids of hyaluronic acid obtained in Comparative Examples 2 to 5. The results tabulated in Table 2.

TABLE 2

Degree of dissolution of hyaluronic acid gel (%)

| Test No. | After 6 hours | After 12 hours | After 24 hours | Remarks |
|---|---|---|---|---|
| 7 | 12 | 14 | 16 | Example 1 |
| 8 | 12 | 16 | 19 | Example 2 |
| 9 | 13 | 22 | 23 | Example 3 |
| 10 | 12 | 15 | 18 | Example 4 |
| 11 | 100 (Completely dissolved) | The same condition as after 6 hours | The same condition as after 6 hours | Comparative Example 2 |
| 12 | 100 (Completely dissolved) | The same condition as after 6 hours | The same condition as after 6 hours | Comparative Example 3 |
| 13 | 100 (Completely dissolved) | The same condition as after 6 hours | The same condition as after 6 hours | Comparative Example 4 |
| 14 | 100 (Completely dissolved) | The same condition as after 6 hours | The same condition as after 6 hours | Comparative Example 5 |

For example, in Test No.7, the degree of dissolution of the hyaluronic acid gel obtained in Example 1 was found to be 14% after 12 hours and 16% after 24 hours. Namely, 84% of the hyaluronic acid remained even after 24 hours. In contrast, in Test No.11, the degree of dissolution of the cast film of about 100 μm thick obtained in Comparative Example 2 was found to be 100% after 6 hours, which indicates complete dissolution.

Thus, it was found that the solids of hyaluronic acid obtained in Comparative Examples dissolved in water quite quickly (Tests Nos.11 to 14), whereas the hyaluronic acid gels obtained in accordance with the present invention dissolved quite slowly (for example, Tests Nos. 7 to 10). These results suggest that the hyaluronic acid gel obtained according to the present invention has a long in vivo residence time.

EXAMPLE 8

Solubilization Test for Hyaluronic Acid Gels

The pH of distilled water was adjusted to 1.5 with hydrochloric acid. The spongy hyaluronic acid gel obtained in Example 1 was washed with distilled water, then washed in the phosphate buffer-physiological saline mentioned in Example 6 and washed with distilled water. The washed hyaluronic acid gel was freeze-dried. The resulting hyaluronic acid gel was immersed in 15 ml of the aqueous solution at pH 1.5, based on 15 mg of dry hyaluronic acid. The solution was left in an oven set at 60° C. 0.5 ml samples were withdrawn after 2 hours, after 6 hours and after 12 hours. After 6 hours, the hyaluronic acid gel had disappeared almost completely and was not visually recognizable.

COMPARATIVE EXAMPLE 6

Sodium hyaluronate with a molecular weight of $2 \times 10^6$ Da was dissolved in distilled water to give a 0.1 wt % hyaluronic acid aqueous solution. The pH of the aqueous solution was adjusted to 1.5 with 1N hydrochloric acid. A 15 ml portion of the acidic hyaluronic acid aqueous solution was left in an oven at 60° C. for 4 hours for acid hydrolysis of the linear hyaluronic acid.

EXAMPLE 9

Measurement of Molecular Weight and Branching Degree of Solubilized Hyaluronic Acid For GPC-MALLS measurement, the solubilized hyaluronic acid obtained in Example 8 and the acid hydrolysate of linear hyaluronic acid obtained in Comparative Example 6 were diluted by a factor of 2 with the GPC eluent to 0.05 wt % and filtered through a membrane filter of 0.2 $\mu$m, and 0.1 ml portions of them were injected.

The measurement was carried out by using a GPC column SB806HQ (Showa Denko K.K.), a differential refractometer 830-RI (JASCO Corporation) as a detector, a MALLS DAWNDSP-F (Wyatt), 0.2M aqueous sodium nitrate as the eluent at a temperature of 40° C. at a flow rate of 0.3 ml/min at intervals of 1 datum/2 sec. For the measurement of the intensity of scattering, eight detectors with scattering angles from 21.7° to 90° were used. For data processing, software ASTRA Version 4.10 (Wyatt) was used.

As described above, the solubilized hyaluronic acid obtained in Example 8 and the acid hydrolysate of linear hyaluronic acid obtained in Comparative Example 6 were examined. The results are shown in Table 3.

TABLE 3

| Test No. | Reaction Time (hour) | Weight-average molecular weight | Molecular weight distribution Mw/Mn | Degree of solubilization (%) | Remarks |
|---|---|---|---|---|---|
| 15 | 2 | 36.8 × 10⁴ | 1.8 | 28 | Example 8 |
| 16 | 6 | 37.8 × 10⁴ | 2.4 | 86 | Example 8 |
| 17 | 12 | 10.7 × 10⁴ | 1.8 | 97 | Example 8 |
| 18 | 4 | 24.7 × 10⁴ | 1.6 | — | Comparative Example 6 |

For example, in Test No.15, it was found that the hyaluronic acid gel obtained in Example 8 was solubilized to a low degree when withdrawn after 2 hours of reaction. In Test No.17, the sample withdrawn after 12 hours of reaction showed such a low molecular weight that the branching degree was difficult to measure. In Test No.16, the hyaluronic acid gel was solubilized to a high degree when withdrawn after 6 hours of reaction, and the large molecular weight distribution of 2.4 reflects the presence of branched hyaluronic acid.

Figure 2:
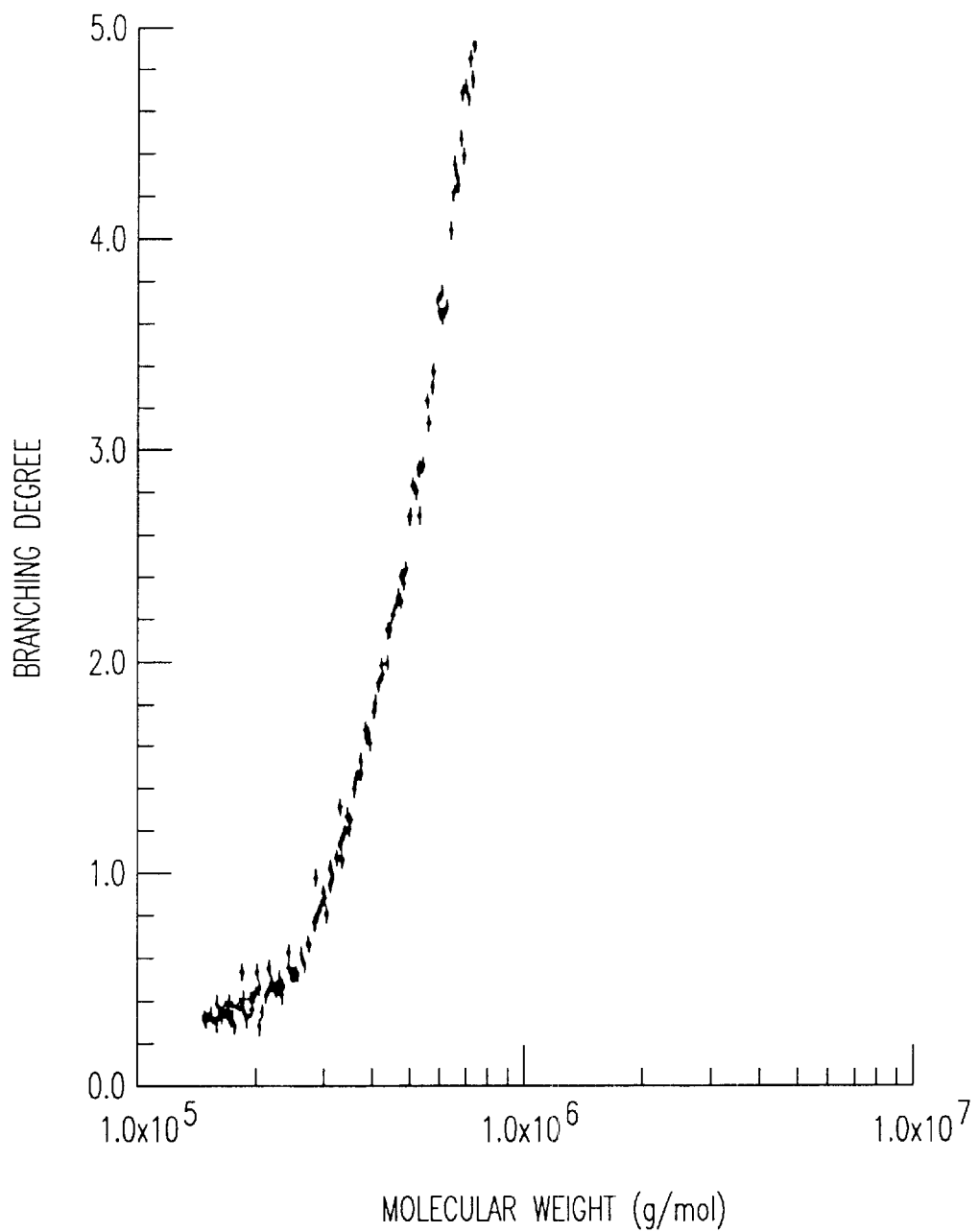
FIG. 2 is a graph that shows the relation between the branching degree and the molecular weight in Example 8 on the basis that the hyaluronic acid in Comparative Example 6 was linear.

The GPC chromatograms of the solubilized hyaluronic acid obtained in Example 8 after 6 hours of reaction and the acid hydrolysate of linear hyaluronic acid obtained in Comparative Example 6, and the results of calculation of their branching degrees obtained in Test No. 16 and Test No.18, respectively, were shown in FIG. 1 and FIG. 2.

As is evident from FIG. 1, the GPC chromatogram 1 for Example 8 had a shoulder at a higher molecular weight range than the GPC chromatogram 2 for Comparative Example 6. From comparison of the molecular weights of fractions at the same elution volumes, it was found that the molecular weight for Example 8 was clearly higher than that for Comparative Example 6 within the elution volume range of at most 8.6 ml, which corresponds to the molecular weight range of about 200,000 or larger.

The fractions for Example 8 showed higher molecular weights than the fractions for Comparative Example 6 at the same elution volumes, because of the presence of branched hyaluronic acid.

FIG. 2 shows the relation of the branching degree and the molecular weight for Example 8 calculated on the basis of the linear hyaluronic acid of Comparative Example 6. The branching degree was calculated from the molecular weights of fractions for Example 8 and Comparative Example 6 at the same elution volumes by using equations (2) and (3).

FIG. 2 shows a sharp rise in the branching degree from 0.5 within the molecular weight range of 200,000 or larger for Example 8, which indicates that the hyaluronic acid gel obtained according to the present invention contains a crosslinked structure stable under accelerating conditions for acid hydrolysis of hyaluronic acid.

EXAMPLE 10

Immersion Test for Hyaluronic Acid Gels in an Alkaline Buffered Aqueous Solution The spongy hyaluronic acid gel obtained in Example 1 was washed with distilled water, then washed in the phosphate buffer-physiological saline mentioned in Example 6, and washed with distilled water. The washed hyaluronic acid gel immersed and left in 50 ml, based on 150 mg of dry hyaluronic acid in the gel, of 25 mM disodium hydrogenphosphate-sodium hydroxide buffer at pH 11 at 25° C., and as a result, the gel dissolved quickly and completely dissolved in 1 hour. Similarly, when the gel was immersed in 25 mM sodium hydrogencarbonate-sodium hydroxide buffer at pH 10, it lost shape in 7 hours and completely dissolved in 18 hours.

It was found that the hyaluronic acid gel obtained according to the present invention had a feature that it is hardly soluble in a neutral aqueous solution but dissolves quickly in an alkaline aqueous solution.

EXAMPLE 11

Measurement of the Swelling Ratio of a Hyaluronic Acid Gel

The spongy hyaluronic acid gel obtained in Example 1 was washed with distilled water, then washed in the phosphate buffer-physiological saline mentioned in Example 6 and washed with distilled water. Then, the washed hyaluronic acid gel was freeze-dried.

100 mg, on a dry basis, of the hyaluronic acid gel was immersed in 200 ml of distilled water and left to stand at 25° C. for 24 hours. The swollen hyaluronic acid gel was withdrawn, drained on filter paper and weighed. The swelling ratio was 117.

The hyaluronic acid gel obtained according to the present invention was found to have a measurably stable swelling ratio.

EXAMPLE 12

Test on Cytotoxicity of a Hyaluronic Acid Gel

The cytotoxicity of the hyaluronic acid gel obtained according to the present invention was evaluated by observing the proliferation behavior of a normal human skin-derived fibroblast culture in the presence of the hyaluronic acid gel obtained according to the present invention without contact between them. The spongy hyaluronic acid gel obtained in Example 1 was freeze-dried in the same manner as in Example 8. The freeze-dried gel was mechanically pulverized, and 20 mg of the pulverized gel was loaded on a cell culture insert (pore size: 3 µm, Falcon) and immersed in the cell culture. For a control experiment, incubation was carried out in the absence of the hyaluronic acid.
Incubation conditions Plate: 12-well plate for cell culture Medium: PDMEM medium+10% fetal bovine serum, 2 ml/well Temperature: 37.5° C. (under 5% $CO_2$)

Cell number: $1 \times 10^4$ cells/well

After 2, 5 and 8 days of incubation, the cell culture was examined on the cell density under an inverted microscope. As a result, it was found that the cell culture had grown in the presence of the hyaluronic acid gel as satisfactorily as that in the control experiment, and thereby it was ascertained that the hyaluronic acid gel obtained according to the present invention had no cytotoxicity.

EXAMPLE 13

Sodium hyaluronate with a molecular weight of $2 \times 10^6$ Da was dissolved in distilled water to give a 1 wt % hyaluronic acid aqueous solution. The pH of the aqueous solution was adjusted to 1.5 with 1N hydrochloric acid to give an acidic hyaluronic acid aqueous solution. A 25 ml portion of the acidic hyaluronic acid aqueous solution was put in a plastic Petri dish and placed in a refrigerator set at −20° C. 22 hours of freezing and 2 hours of thawing at 25° C. were repeated twice to give a spongy hyaluronic acid gel. Then, the gel was immersed for neutralization at 5° C. for 24 hours in 100 ml of a phosphate buffer-physiological saline at pH 7 prepared by adding a phosphate buffer to physiological saline to a concentration of 50 mM, and washed thoroughly with distilled water. The gel was pressed between two plates and freeze-dried to give an adhesion preventive sheet made of a hyaluronic acid gel.

EXAMPLE 14

The procedure in Example 13 was followed except that sodium hyaluronate with a molecular weight of $6 \times 10^5$ Da was used to give an adhesion preventive sheet made of a hyaluronic acid gel.

EXAMPLE 15

A 25 ml portion of the acidic aqueous solution of hyaluronic acid with a molecular weight of $2 \times 10^6$ Da at pH 1.5 prepared in Example 13 was put in a plastic Petri dish and placed in a refrigerator set at −20° C. 22 hours of freezing and 2 hours of thawing at 25° C. were repeated twice to give a spongy hyaluronic acid gel. Then, the gel was immersed in a phosphate buffer-physiological saline, washed and pressed between two plates in the same manners as in Example 13. Then, the gel was air-dried at 30° C. for 3 hours to give an adhesion preventive film made of a hyaluronic acid gel.

EXAMPLE 16

50 mg of the hyaluronic acid sheet obtained in Example 13 was aseptically crushed in 10 ml of physiological saline in a microhomogenizer (POLYTORON, KINIMATICA AG) to give a flaky adhesion preventive made of a hyaluronic acid gel.

EXAMPLE 17

A 15 ml portion of the acidic aqueous solution of hyaluronic acid with a molecular weight of $2 \times 10^6$ Da at pH 1.5 prepared in Example 13 was put in a 30 ml vessel and placed in a refrigerator set at −20° C. 22 hours of freezing and 2 hours of thawing at 25° C. were repeated twice to give a spongy hyaluronic acid gel. Then, the gel was immersed for neutralization at 5° C. for 24 hours in 100 ml of a phosphate buffer-physiological saline at pH 7 prepared by adding a phosphate buffer to physiological saline to a concentration of 50 mM, and washed thoroughly with distilled water. The gel was directly freeze-dried to give an adhesion preventive sponge made of a hyaluronic acid gel.

EXAMPLE 18

A 15 ml portion of the acidic aqueous solution of hyaluronic acid with a molecular weight of $2 \times 10^6$ Da at pH 1.5 prepared in Example 13 was put in a 30 ml vessel and placed in a refrigerator set at −20° C. 22 hours of freezing and 2 hours of thawing at 25° C. were repeated twice to give a spongy hyaluronic acid gel. The gel was immersed in a phosphate buffer-physiological saline and washed in the same manners as in Example 13, then drained by centrifugation and freeze-dried in the compacted state to give a biomedical mass made of a hyaluronic acid gel.

EXAMPLE 19

Sodium hyaluronate with a molecular weight of $2 \times 10^6$ Da was dissolved in distilled water at a concentration of 0.05%, and the pH was adjusted to 1.5 with 1N hydrochloric acid. A 100 ml portion of the acidic hyaluronic aid aqueous solution was put in a 200 ml vessel and placed in a refrigerator set as −20° C.

22 hours of freezing and 2 hours of thawing at 25° C. were repeated twice to give a fibrous hyaluronic acid gel. The gel was collected by filtration, then immersed in a phosphate buffer-physiological saline, washed and freeze-dried in the same manners as in Example 13 to give a fibrous biomedical material made of a hyaluronic acid gel.

EXAMPLE 20

A 5 ml portion of the acidic solution of hyaluronic acid with a molecular weight of $2 \times 10^6$ Da at pH 1.5 prepared in Example 13 was poured into a tubular mold and placed in a refrigerator set as −20° C. 22 hours of freezing and 2 hours of thawing at 25° C. were repeated twice to give a tubular hyaluronic acid gel. The gel was immersed in a phosphate buffer-physiological saline, washed and freeze-dried in the same manners as in Example 13 to give a biomedical tube made of a hyaluronic acid gel.

EXAMPLE 21

A 25 ml portion of the acidic solution of hyaluronic acid with a molecular weight of $2 \times 10^6$ Da at pH 1.5 prepared in Example 13 was put in a plastic Petri dish and placed in a refrigerator set as $-20°$ C. 22 hours of freezing and 2 hours of thawing at $25°$ C. were repeated twice to give a spongy hyaluronic acid gel. The gel was immersed in a phosphate buffer-physiological saline and washed in the same manners as in Example 13. After mild drainage, the gel was impregnated with 5 ml of a 1 wt % hyaluronic acid aqueous solution, pressed between two plates and freeze-dried to give an adhesion preventive sheet of a hyaluronic acid gel coupled with hyaluronic acid.

COMPARATIVE EXAMPLE 7

The hyaluronic acid aqueous solution prepared in Example 13 was adjusted to pH 7.0 with 1N sodium hydroxide, and a 25 ml portion of the solution was frozen at $-20°$ C. and freeze-dried in a plastic Petri dish to give a hyaluronic acid sheet.

COMPARATIVE EXAMPLE 8

The hyaluronic acid aqueous solution prepared in Example 13 was adjusted to pH 7.0 with 1N sodium hydroxide, and a 25 ml portion of the solution was air-dried at $60°$ C. in a plastic Petri dish to give a hyaluronic acid sheet.

COMPARATIVE EXAMPLE 9

The hyaluronic acid aqueous solution prepared in Example 13 was adjusted to pH 7.0 with 1N sodium hydroxide, and a 25 ml portion of the solution was frozen at $20°$ C. and freeze-dried in a beaker to give a hyaluronic acid sponge.

COMPARATIVE EXAMPLE 10

In a solution of 1.1 g of disodium hydrogenphosphate hydrate in 30 g of water adjusted to pH 10 with 2% sodium hydroxide, 0.6 g of sodium hyaluronate with a molecular weight of $6 \times 10^5$ Da was dissolved. Then, 0.05 g of cyanuric chloride in 1.5 ml of dioxane was added to the above-mentioned hyaluronic acid solution, and the reaction was carried out at room temperature for 3 hours. Then, the reaction solution was put into a dialysis membrane, dialyzed against water for 1 day, poured onto a framed glass plate and dried to give a film.

EXAMPLE 22

Solubility Test on Adhesion Preventives Biomedical Materials Made of Hyaluronic Acid Gels A 50 mM phosphate buffer-physiological saline at pH 7 was prepared by adding a phosphate buffer to physiological saline. Adhesion preventives and biomedical materials made of hyaluronic acid gels containing 150 mg of hyaluronic acid on a dry basis were gently shaken in 50 ml of the phosphate buffer-physiological saline. The solubilities of the adhesion preventives and biomedical materials made of hyaluronic acid gels in the phosphate buffer-physiological saline at $25°$ C. were evaluated from their shapes.

As described above, the solubility test was actually carried out on the adhesion preventives and biomedical materials made of hyaluronic acid gels obtained in Examples 13 to 21 and comparative Examples 7 to 9. The results are shown in Table 4.

TABLE 4

Shape of adhesion preventives and biomedical material made of hyaluronic acid

| Test No. | After 1 day | After 4 days | After 7 days | Remarks |
|---|---|---|---|---|
| 19 | Not changed | Not changed | Partly dissolved | Example 13 |
| 20 | Not changed | Partly dissolved | Partly dissolved | Example 14 |
| 21 | Not changed | Not changed | Partly dissolved | Example 15 |
| 22 | Not changed | Partly dissolved | Partly dissolved | Example 16 |
| 23 | Not changed | Not changed | Not changed | Example 17 |
| 24 | Not changed | Not changed | Not changed | Example 18 |
| 25 | Not changed | Not changed | Partly dissolved | Example 19 |
| 26 | Not changed | Not changed | Partly dissolved | Example 20 |
| 27 | Not changed | Partly dissolved | Partly dissolved | Example 21 |
| 28 | Completely dissolved | The same as the state after 1 day | The same as the state after 1 day | Comparative Example 7 |
| 29 | Completely dissolved | The same as the state after 1 day | The same as the state after 1 day | Comparative Example 8 |
| 30 | Completely dissolved | The same as the state after 1 day | The same as the state after 1 day | Comparative Example 9 |

As shown in Table 4, the adhesion preventives and biomedical materials made of hyaluronic acid gels obtained in Examples (Tests Nos.19 to 27) did not change or partly dissolved in 7 days in the neutral aqueous solution at $25°$ C. and were able to keep their shapes for at least 1 day, whereas the mere molded sheets and sponges of hyaluronic acid obtained in Comparative Examples (Tests Nos.28 to 30) dissolved completely in 1 day.

EXAMPLE 23

Solubility Test on Adhesion Preventives Biomedical Materials Made of Hyaluronic Acid Gels A 50 mM phosphate buffer-physiological saline at pH 7 was prepared by adding a phosphate buffer to physiological saline. Adhesion preventives and biomedical materials made of hyaluronic acid gels containing 150 mg of hyaluronic acid on a dry basis were gently shaken in 50 ml of the phosphate buffer-physiological saline. The proportions of the hyaluronic acid dissolved in the phosphate buffer-physiological saline at $37°$ C. were calculated from the hyaluronic acid concentrations of the phosphate buffer-physiological saline.

Measurement of Hyaluronic Acid Concentration

The concentration of hyaluronic acid in the phosphate buffer-physiological saline was obtained from the area of a GPC peak by using a differential refractometer as a detector.

As described above, the solubility test was actually carried out on the adhesion preventives and biomedical materials made of hyaluronic acid gels obtained in Examples 13 to 21 and Comparative Examples 7 to 9. The results are shown in Table 5.

TABLE 5

Degree of dissolution of adhesion preventive and biomedical material made of hyaluronic acid (%)

| Test No | After 12 hours | After 1 day | After 4 days | After 7 days | Remarks |
|---|---|---|---|---|---|
| 31 | 6 | 15 | 24 | 29 | Example 13 |
| 32 | 15 | 21 | 38 | 55 | Example 14 |
| 33 | 6 | 18 | 26 | 35 | Example 15 |
| 34 | 8 | 21 | 29 | 40 | Example 16 |
| 35 | 8 | 16 | 22 | 28 | Example 17 |
| 36 | 6 | 15 | 20 | 26 | Example 18 |
| 37 | 8 | 15 | 26 | 32 | Example 19 |
| 38 | 8 | 14 | 24 | 30 | Example 20 |
| 39 | 12 | 21 | 30 | 36 | Example 21 |
| 40 | 100 | 100 | 100 | 100 | Comparative Example 7 |
| 41 | 100 | 100 | 100 | 100 | Comparative Example 8 |
| 42 | 96 | 100 | 100 | 100 | Comparative Example 9 |

As shown in Table 5, the adhesion preventives and biomedical materials made of hyaluronic acid gels obtained in Examples (Tests Nos.31 to 39) dissolved to degrees of dissolution of 26 to 55% in 7 days in the neutral aqueous solution at 25° C. and were hardly soluble, whereas the mere molded sheets and sponges of hyaluronic acid obtained in Comparative Examples (Tests Nos.40 to 42) dissolved to degrees of 96 to 100% in 12 hours.

EXAMPLE 24

Biocompatibility Test and In Vivo Persistency Test on Adhesion Preventive Hyaluronic Acid Gels For the following test, the adhesion preventive hyaluronic acid sheets obtained in Examples 13 and 14 cut into 1 cm×1 cm squares, and as controls, the hyaluronic acid sheet obtained in Comparative Example 7 and the cyanuric chloride-crosslinked hyaluronic acid obtained in Comparative Example 10 were cut into 1 cm×1 cm squares.

Five of twenty 12-week-old female DDY mice (average body weight 33 g) were used for implantation of the hyaluronic acid gel (molecular weight 2×10$^6$ Da), five for implantation of the hyaluronic acid gel (molecular weight 6×10$^5$ Da), and in comparative tests, five were used for the freeze-dried hyaluronic acid, and the remaining five for the cyanuric chloride-crosslinked hyaluronic acid.

In the implantation, mice were cut about 1.5 cm long along the ventrimeson under a nembutal anesthetic and then sutured with various kinds of hyaluronic acid placed on the appendices.

3, 5, 7, 9 and 14 days after the implantation, one of the mice implanted with each kind of hyaluronic acid gel and freeze dried hyaluronic acid was killed by cervical dislocation and cut on the abdomen. Then, the state of the implantation site was observed. Then, the inside of the intraperitoneal cavity was washed with physiological saline to recover the remaining hyaluronic acid, inclusive of the residue of the hyaluronic acid sheet.

The recovered washings were mixed with the equal amount of 0.02N sodium hydroxide, then left to stand for 1 hour and neutralized with hydrochloric acid. They were subsequently centrifuged and filtered through a filter (pore size 0.45 μm) to give. The resulting samples were analyzed by GPC to determine hyaluronic acid in the samples. The recoveries of hyaluronic acid based on the hyaluronic acid in the implanted sheets were calculated and shown in Table 6 together with the results of the observation of the states of the implantation sites.

TABLE 6

| Test No. | Implanted sheet | Days of implantation | Recovery of hyaluronic acid (%) | State of sheet | State of tissue |
|---|---|---|---|---|---|
| 43 | Hyaluronic acid of Example 13 (M.W. 2 × 10$^6$) | 3 | 83 | Original shape | ○ |
|  |  | 5 | 63 | Original shape | ○ |
|  |  | 7 | 28 | Fragmented | ○ |
|  |  | 9 | 15 | Small residue | ○ |
|  |  | 14 | 0 | Undetectable | ○ |
| 44 | Hyaluronic acid of Example 14 (M.W. 6 × 10$^5$) | 3 | 59 | Original shape | ○ |
|  |  | 5 | 13 | Small residue | ○ |
|  |  | 7 | 2 | Small residue | ○ |
|  |  | 9 | 0 | Undetectable | ○ |
|  |  | 14 | 0 | Undetectable | ○ |
| 45 | Freeze dried hyaluronic acid of Comparative Example 7 | 3 | 0 | Undetectable | ○ |
|  |  | 5 | 0 | Undetectable | ○ |
|  |  | 7 | 0 | Undetectable | ○ |
|  |  | 9 | 0 | Undetectable | ○ |
|  |  | 14 | 0 | Undetectable | ○ |
| 46 | Cyanuric chloride-crosslinked hyaluronic acid of Comparative Example 10 | 3 | 73 | Original shape | Δ |
|  |  | 5 | 46 | Original shape | Δ |
|  |  | 7 | 10 | Small residue | Δ |
|  |  | 9 | 0 | Undetectable | Δ |
|  |  | 14 | 0 | Undetectable | Δ |

○: normal
Δ: slight inflammation

Although all the mice grew normally, slight inflammation was observed on the tissues implanted with cyanuric chloride-crosslinked hyaluronic acid obtained in Comparative Example 10, whereas the tissues implanted with the hyaluronic acid gels and the freeze dried hyaluronic acid were normal.

EXAMPLE 25

Test on Adhesion Preventive Effect of Adhesion Preventive Hyaluronic Acid Gels Using a Mouse Uterine Model For the following test, the adhesion preventive hyaluronic acid gel obtained in Example 13 was cut into 1 cm×2 cm rectangles, and similarly the adhesion preventive hyaluronic acid gel obtained in Example 13 impregnated with the hyaluronic acid solution prepared in Example 13 and as controls, the hyaluronic acid sheet obtained in Comparative Example 7, the hyaluronic acid solution prepared in Example 13 and the cyanuric chloride-crosslinked hyaluronic acid obtained in Comparative Example 10 were cut into 1 cm×2 cm rectangles.

7-week-old female ICR mice (body weight 25 to 30 g) were anesthetized by intraperitoneal pentobarbital injection and cut along the ventrimeson. Then, an abrasion of about 10 cm long was made on the uterine horn of each mouse by application of iodine. Ten mice were allotted to each treatment group. The above-mentioned 1 cm×2 cm rectangular sheets of a hyaluronic acid gel, hyaluronic acid or cyanuric chloride-crosslinked hyaluronic acid or nothing, for control test, were wrapped around the abrasions. In the case of the hyaluronic acid solution, a 1 ml portion of the hyaluronic acid solution prepared in Example 13 was applied to each abrasion. In the case of the combined use of the hyaluronic acid gel and the hyaluronic acid solution, the hyaluronic acid gel was wrapped around the abrasions first, and the hyaluronic acid solution was added to the intraperitoneal cavity. In any case, 5-0 Dexon was used for closure.

10 days later, each group of mice, which were not treated or treated with the hyaluronic acid gel, the combination of the hyaluronic acid gel and the hyaluronic acid solution, the hyaluronic acid sheets, the hyaluronic acid solution or the cyanuric chloride-crosslinked hyaluronic acid, were sacrificed by cervical dislocation. Then ventrotomy was performed again, and inspection for adhesions was carried out. In the judgement of formation of an adhesion, very slight membranous adhesions were excluded, and only fibrous and thick adhesions strong enough not to peel off even if pulled with tweezers were counted in. The results are shown in Table 7.

TABLE 7

| Test No. | Group | Adhesion formation ratio | Remarks |
|---|---|---|---|
| 47 | No treatment | 9/10 | Comparative Example |
| 48 | Hyaluronic acid gel of Example 13 | 1/10 | Example |
| 49 | Hyaluronic acid gel of Example 13 and hyaluronic acid solution prepared in Example 13 | 0/10 | Example |
| 50 | Hyaluronic acid sheet of Comparative Example 7 | 5/10 | Comparative Example |
| 51 | Hyaluronic acid solution prepared in Example 13 | 6/10 | Comparative Example |
| 52 | Cyanuric chloride-crosslinked hyaluronic acid of Comparative Example 10 | 3/10 | Comparative Example |

As shown in FIG. 7, formation of adhesions was recognized in nine of the ten non-treated mice, in five of the ten treated with the mere hyaluronic acid sheets, in six of the ten treated with the hyaluronic acid solution and three of the ten treated with the cyanuric chloride-crosslinked hyaluronic acid, whereas the adhesion preventive hyaluronic acid gel prepared in Example 13 and the combination of the adhesion preventive hyaluronic acid gel prepared in Example 13 and the hyaluronic acid solution prepared in Example 13 developed adhesions in one and none, respectively, of the mice treated. Thus, it was suggested that the adhesion preventive hyaluronic acid gel prepared in Example 13 and the combination of the adhesion preventive hyaluronic acid gel prepared in Example 13 and the hyaluronic acid solution prepared in Example 13 have strong adhesion preventive effect.

EXAMPLE 26

Adhesion Preventive Test of Adhesion Preventive Hyaluronic Acid Gels on a Rat Cecal Model For the following test, the adhesion preventive hyaluronic acid gel obtained in Example 13, and as controls, the hyaluronic acid sheet obtained in Comparative Example 7 and the cyanuric chloride-crosslinked hyaluronic acid were cut into 2 cm×2 cm squares.

10-week-old male Wister rats (body weight about 250 g) were anesthetized with ketamine (60 mg/1 kg body weight) and xylazine (10 mg/1 kg body weight) intraperitoneally and cut along the ventrimeson. The ceca were abraded over about 10 cm×10 cm with a gauge (about 20 times) to develop abrasions with blood spots. In each group of five rats, the abrasions were covered with nothing (control), or the above-mentioned 2 cm×2 cm rectangular sheets of the hyaluronic acid gel, hyaluronic acid or cyanuric chloride-crosslinked hyaluronic acid, and closure was performed by using 3-0 Dexon.

14 days later, the five rats in each group treated with nothing, the hyaluronic acid gel, the hyaluronic acid sheet or the cyanuric chloride-crosslinked hyaluronic acid were sacrificed. Then ventrotomy was performed again, and inspection for adhesions was carried out. In the judgement of formation of an adhesion, very slight membranous adhesions were excluded, and only fibrous and thick adhesions strong enough not to peel off even if pulled with tweezers were counted in. The results are shown in Table 8.

TABLE 8

| Test No. | Group | Adhesion formation ratio | Remarks |
|---|---|---|---|
| 53 | No treatment | 4/5 | Comparative Example |
| 54 | Hyaluronic acid gel of Example 13 | 1/5 | Example |
| 55 | Hyaluronic acid sheet of Comparative Example 7 | 3/5 | Comparative Example |
| 56 | Cyanuric chloride-crosslinked hyaluronic acid of Comparative Example 10 | 2/5 | Comparative Example |

As shown in FIG. 8, formation of adhesions was recognized in four of the five non-treated rats, in three of the five treated with the mere hyaluronic acid sheets, and in two of the ten treated with the cyanuric chloride-crosslinked hyaluronic acid, whereas the adhesion preventive hyaluronic acid gel prepared in Example 13 developed adhesions in one of the rats treated.

As described above, according to the present invention, it is possible to obtain a hyaluronic acid gel hardly soluble in water without using any chemical crosslinkers or chemical modifiers. The adverse effects on biocompatibility attributable to chemical crosslinkers or chemical modifiers are avoided, and the hyaluronic acid gel is useful in the field of biocompatible materials by virtue of its long in vivo residence time. In particular, the hyaluronic acid gel which is hardly soluble in water can provide an excellent adhesion preventive which (1) has ideal in vivo persistency as an adhesion preventive, (2) prevents effectively postoperative adhesion by virtue of the drastically improved residence time on wounds, and (3) is so safe as to thoroughly solve the problems of conventional chemically modified hyaluronic acid with toxicity and biocompatibility.

What is claimed is:

1. A gel comprising hyaluronic acid, or its alkali metal salt, said gel prepared by at least once freezing and subsequently thawing a hyaluronic acid aqueous solution at a pH of 3.5 or below, which has not been subjected to chemical crosslinking by a chemical crosslinking compound other than hyaluronic acid or chemical modification by a chemical modifying compound other than hyaluronic acid, and which is not in the form of a complex with a cationic polymer and (1) which dissolves in a neutral aqueous solution at 25° C. in one day to a degree of dissolution of at most 50%, or (2) which dissolves in a neutral aqueous solution at 37° C. in 12 hours to a degree of dissolution of at most 50%, or both (1) and (2).

2. The hyaluronic acid gel according to claim 1, which keeps its shape for at least one day in a neutral aqueous solution at 25° C.

3. The hyaluronic acid gel according to claim 1, which is obtained by acid hydrolysis of hyaluronic acid under conditions wherein said hyaluronic acid gel dissolves to yield solubilized hyaluronic acid having a branched structure and containing a molecular weight fraction with a branching degree of at least 0.5.

4. The hyaluronic acid gel according to claim 3, wherein said conditions comprise a pH of an aqueous solution to be 1.5 and a temperature of 60° C.

5. A biomedical material containing a gel made of hyaluronic acid or its alkali metal salt, said gel prepared by at least once freezing and subsequently thawing a hyaluronic acid aqueous solution at a pH of 3.5 or below, wherein said gel has not been subjected to chemical crosslinking by a chemical crosslinking compound other than hyaluronic acid or chemical modification by a chemical modifying compound other than hyaluronic acid, and which is not in the form of a complex with a cationic polymer which satisfies the following requirements (a) and (b):

(a) the hyaluronic acid gel dissolves in a neutral aqueous solution at 25° C. in one day to a degree of dissolution of at most 50%, and (b) the gel is obtained by acid hydrolysis of hyaluronic acid under conditions such that said hyaluronic acid gel dissolves to yield solubilized hyaluronic acid having a branched structure and containing a molecular weight fraction with a branching degree of at least 0.5.

6. The biomedical material according to claim 5, wherein the gel made of hyaluronic acid is in the form of a sheet, a film, a flake, a sponge, a mass, a fiber or a tube.

7. The biomedical material according to claim 5, which is an adhesion preventive.

8. A biomedical material containing a hyaluronic acid, or its alkali metal salt, gel and an un-gelled hyaluronic acid, said gel prepared by at least once freezing and subsequently thawing a hyaluronic acid aqueous solution at a pH of 3.5 or below and wherein said gel has not been subjected to chemical cross-linking by a chemical cross-linking compound other than hyaluronic acid or chemical modification by a chemical modifying compound other than hyaluronic acid, and said gel is not in the form of a complex with a cationic polymer, wherein the hyaluronic acid gel dissolves in a neutral aqueous solution at most 50%, and the hyaluronic acid gel is obtained by acid hydrolysis of hyaluronic acid under conditions such that said hyaluronic acid gel dissolves to yield solubilized hyaluronic acid having a branched structure and containing a molecular weight fraction with a branching degree of at least 0.5.

9. A biomedical material according to claim 8, wherein said conditions comprise a pH of an aqueous solution to be 1.5 and a temperature of 60° C.

10. A biomedical material containing, in the form of a sheet, a film, a flake, a sponge, a mass, a fiber or a tube, (1) hyaluronic acid gel made of hyaluronic acid, or its alkali metal salt, said gel prepared by at least once freezing and subsequently thawing a hyaluronic acid aqueous solution at a pH of 3.5 or below, and wherein said gel has not been subjected to chemical crosslinking or chemical modification by a compound other than hyaluronic acid, and which is not in the form of a complex with a cationic polymer and (2) an un-gelled hyaluronic acid.

* * * * *